United States Patent [19]

Mandella et al.

[11] Patent Number: 6,075,612
[45] Date of Patent: *Jun. 13, 2000

[54] OPTICAL DEVICES HAVING TOROIDAL MIRRORS FOR PERFORMING REFLECTANCE MEASUREMENTS

[75] Inventors: Michael J. Mandella, Cupertino; Dale H. Buermann, Los Altos; Abdul Rahim Forouhi, Cupertino, all of Calif.

[73] Assignee: n&k Technology, Inc., Santa Clara, Calif.

[*] Notice: This patent is subject to a terminal disclaimer.

[21] Appl. No.: 09/336,605

[22] Filed: Jun. 18, 1999

[51] Int. Cl.$^7$ .............................. G01N 21/55; G01J 3/42
[52] U.S. Cl. .......................................... 356/445; 356/319
[58] Field of Search ...................... 356/319, 445

[56] References Cited

U.S. PATENT DOCUMENTS

| | | | |
|---|---|---|---|
| 4,094,579 | 6/1978 | McMahon et al. | 350/96.17 |
| 4,905,170 | 2/1990 | Forouhi et al. | 364/556 |
| 5,064,283 | 11/1991 | Tober | 356/73 |
| 5,293,216 | 3/1994 | Moslehi | 356/371 |
| 5,483,337 | 1/1996 | Barnard et al. | 356/316 |
| 5,559,597 | 9/1996 | Battey et al. | 356/328 |
| 5,880,831 | 3/1999 | Buermann et al. | 356/319 |

*Primary Examiner*—Frank G. Font
*Assistant Examiner*—Philip Natividad
*Attorney, Agent, or Firm*—Lumen Intellectual Property Services

[57] ABSTRACT

An optical device for measuring reflectance, and, optionally, transmission, of a substrate. The device has first and second toroidal mirrors and first and second optical fibers. The first toroidal mirror directs light from the first optical fiber toward the substrate, which reflects from the substrate and is collected by the second toroidal mirror. The light collected by the second toroidal mirror is focused into the second optical fiber. There are many possible orientations for the fibers and mirrors. The device may also have a fold mirror for directing the light toward the substrate. Optionally, the present invention includes components for measuring transmission of the substrate. The components for measuring transmission may include fibers and toroidal mirrors. Preferably, reflectance and transmission are measured at the same location. If a fold mirror is used, the fold mirror has a gap to allow transmission measurements to be performed at the same location as reflectance measurements. The present invention includes several possible arrangements for fibers and toroidal mirrors.

30 Claims, 8 Drawing Sheets

OPTICAL DEVICES HAVING TOROIDAL MIRRORS FOR PERFORMING REFLECTANCE MEASUREMENTS

FIELD OF THE INVENTION

This invention relates generally to optical measurements. More particularly, it relates to devices for performing accurate reflectance and transmission measurements. The present invention uses toroidal mirrors to improve measurement accuracy, and uses optical fibers for increased flexibility.

BACKGROUND OF THE INVENTION

There are many industrial applications where it is important to accurately measure physical characteristics of thin films. Fabrication of integrated circuits and flat panel displays are two examples. Often it is necessary to measure the thickness, and optical constants n and k of thin films deposited on a substrate.

One known technique for determining many physical characteristics of thin films and materials is disclosed in U.S. Pat. No. 4,905,170 to Forouhi et al. In this technique, and many others, it is necessary to perform accurate, broadband reflectance and/or transmission measurements of the thin films. When performing such measurements, chromatic distortions can lead to inaccurate results. This happens, for example, if a chromatic response (attenuation as a function of wavelength) of the optical system performing the measurements changes between measurements. An example of a change in chromatic response is when an attenuation of a certain wavelength changes more than an attenuation of another wavelength. Any optical system used must have a fixed chromatic response. Systems that use lenses are generally not suitable because the chromatic response of lens-based systems can be altered by very small mechanical misalignments.

U.S. Pat. No. 5,880,831 to Dale H. Buermann, Abdul Rahim Forouhi, and Michael J. Mandella discloses optical systems suitable for use with thin film characterization methods requiring constant chromatic response. The system uses toroidal mirrors. Small misalignments of the surface being analyzed or the mirrors results in only small changes in chromatic response. This property makes mirrors particularly well suited for use in systems requiring fixed chromatic response.

A shortcoming of the systems disclosed in U.S. Pat. No. 5,880,831 is that free-space light propagation is required. This reduces the mechanical flexibility of the system and constrains the system design. For example, if a spectrophotometer is used, it must have a fixed location with respect to the mirrors. Movement of the system to measure different points on a substrate can therefore be problematic. Another shortcoming is that it is often desirable to perform simultaneous reflectance and transmittance (R&T) measurements at the same location. U.S. Pat. No. 5,880,831 does not teach a system for performing simultaneous R&T measurements.

OBJECTS AND ADVANTAGES OF THE INVENTION

Accordingly, it is a primary object of the present invention to provide a optical device that:
1) provides accurate reflectance measurements with fixed chromatic response, and is mechanically flexible;
2) provides accurate and simultaneous R&T measurements with fixed chromatic response, and is mechanically flexible.

These and other objects and advantages will be apparent upon reading the following description and accompanying drawings.

SUMMARY OF THE INVENTION

These objects and advantages are attained by an optical system having a first optical fiber and a first toroidal mirror for receiving a light beam from the first optical fiber. The first toroidal mirror directs the light beam toward a substrate surface. A second toroidal mirror collects light reflected by the substrate surface. A second optical fiber receives light collected by the second toroidal mirror.

Preferably, the light is focused where it reflects from the substrate (i.e., an image of the first optical fiber endface is located at the substrate surface). Preferably, the optical fibers are transparent over the wavelength range 190–1100 nanometers and have an attenuation of less than 5 dB/meter over this range. Also preferably, the light is incident on the substrate at an angle less than 8 degrees from normal.

The optical system can also include components for performing transmission measurements at the spot where light reflects from the substrate. The components for transmission measurements can include toroidal mirrors, lenses, and optical fibers.

The optical system can further include a fold mirror for directing the light beam toward the substrate. This allows increased flexibility of the optical system design. The fold mirror can have a space or hole (i.e., generally a gap). The gap allows a second light beam for transmission measurements to strike the substrate at the same location as the light beam for reflectance measurements. If a fold mirror is used, then the system can have a device for moving the fibers and mirrors with respect to the fold mirror so that adjustable focusing is provided.

DETAILED DESCRIPTION

The present invention provides optical systems for performing reflectance and/or transmission measurements with fixed chromatic response. The systems have toroidal mirrors that provide fixed chromatic response and optical fibers which provide mechanical flexibility. The optical fibers are preferably broadband fibers capable of transmitting a wide range of wavelengths needed for accurate thin film characterization. Fold mirrors can also be used to provide increased design flexibility and size reduction. The present invention is similar to the systems disclosed in U.S. Pat. No. 5,880,831, which is hereby incorporated by reference.

Figure 1:
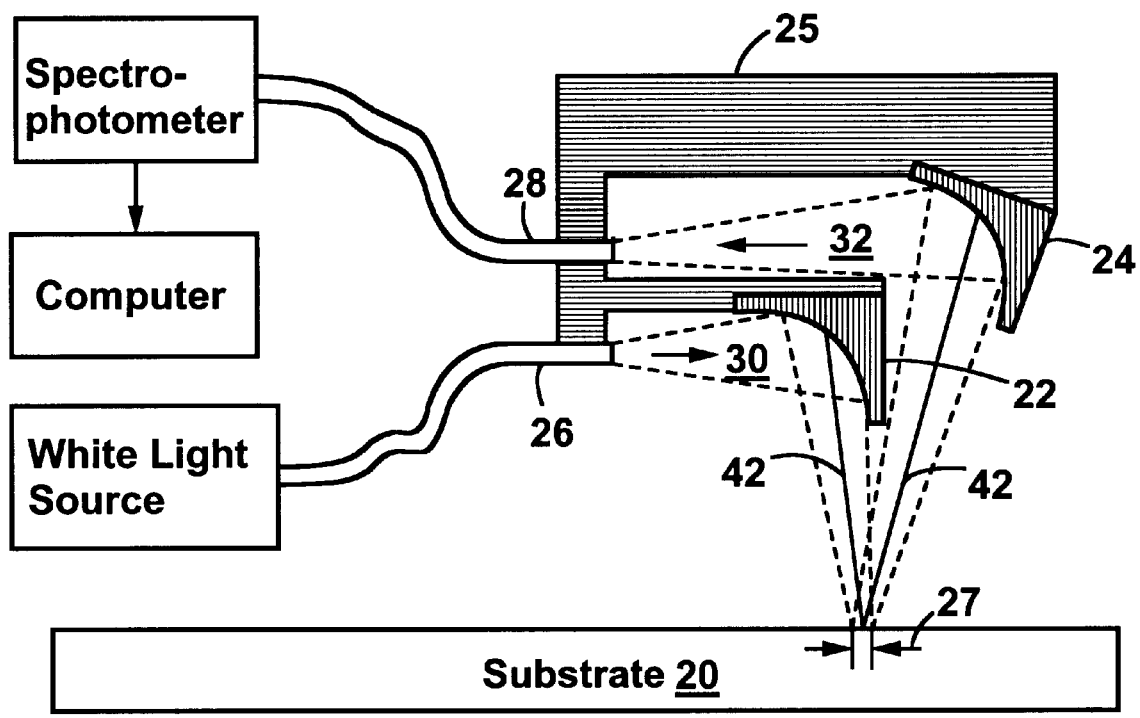
FIG. 1 shows an embodiment of the present invention.

FIG. 1 shows a preferred embodiment of the present invention which can be used for making optical reflectance measurements of a substrate 20. Thin films may be present on the substrate 20. Substrate 20 can be a semiconductor wafer, or an incomplete flat panel display, for example.

The apparatus shown in FIG. 1 has a first toroidal mirror 22 and a second toroidal mirror 24, an input optical fiber 26 and an output optical fiber 28. Preferably, an optical head 25 holds the mirrors 22, 24 and fibers 26, 28 in fixed positions. The first toroidal mirror 22 is located to receive input light 30 from the input fiber, and direct this light to the substrate 20. Reflected light 32 from the substrate 20 is collected by the second toroidal mirror 24 and focused into the output fiber 28. The mirrors 22, 24 may need to be tilted so that light path 42 is not perfectly perpendicular to the substrate 20.

The first toroidal mirror 22 focuses light 30 from input fiber 26 onto substrate 20. Therefore, light 30 is incident upon the substrate 20 in a small spot 27. Preferably, first toroidal mirror 22 focuses light 30 such that input fiber 26 is imaged onto the substrate with unit magnification. In other words, it is preferable for spot 27 to have the same size as the endface of input fiber 26. This alignment is preferred because it reduces the sensitivity of the system to substrate misalignment. For example, if the substrate is tilted slightly, the reflected light 32 is still focused onto the output fiber 28. In a typical implementation, spot 27 and the fiber endface may be about 0.5 millimeter in diameter.

Optionally, if a long working distance is needed between the mirrors 22, 24 and the substrate 20, then the fibers 26, 28 can be moved closer to the mirrors. This provides a larger magnified image of the fiber endface at the substrate 20 (i.e., the spot 27 is bigger). For example, with a magnification of 2, and a fiber endface size of 0.5 millimeter, the spot 27 will be about 1 millimeter in diameter.

Preferably, the optical head can move with respect to the substrate 20. For example, the head 25 can be moved perpendicular to substrate 20 to accommodate substrates of different thicknesses. Also, the head 25 may move across the substrate to perform measurements at different locations on the substrate.

Figure 2:
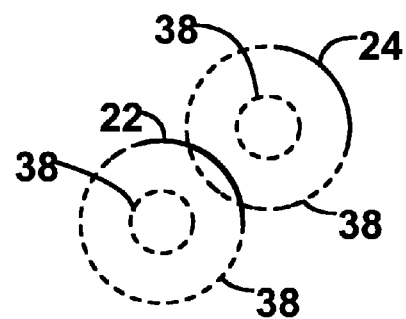
FIG. 2 illustrates the orientation of toroidal mirrors in the present invention.

FIG. 2 shows a view of the system illustrating the orientation of the toroidal mirrors. Dashed lines 38 represent the toroidal surfaces defined by the toroidal mirrors 22, 24.

Input fiber 26 is preferably connected to a white light source 34 (i.e. a broad band light source) so that light 30 is broad band. Output fiber is preferably connected to a spectrophotometer 36 for analyzing reflected light 32. In operation, white light is focused onto the substrate 20, reflected, collected by second mirror 24 and sent to the spectrophotometer 36. The spectrophotometer provides a measurement of substrate reflectance as a function of wavelength. The spectrophotometer communicates with a computer which calculates optical constants n and k based on the reflectance spectrum.

Fibers 28, 28 are preferably large-core multimode fibers capable of transmitting a wide range of wavelengths with low attenuation. The fibers can have a core of about 100–1000 microns, for example. A large core is preferred because it helps to reduce changes in chromatic response which can be caused by mechanical misalignments between fibers 26, 28 and mirrors 22, 24, or by misalignment of the substrate. A large core helps to assure that different wavelengths have uniform mode distributions inside the fibers. Single mode fibers can also be used if measurements at only one wavelength are desired. Also, a combination of single-mode and multimode fibers can be used if it is desirable to perform a number of measurements simultaneously.

Also, certain combinations of core sizes (for input fiber 26 and output fiber 28) can improve the chromatic response stability of the system when subjected to mechanical misalignments of substrate or mirrors. For example if a small (e.g. 200 micron diameter) input fiber 26 is used, and a large (e.g. 1000 micron diameter) output fiber 28 is used, then the stability of the system is improved. The reflected light 32 is imaged onto the output fiber endface to a spot size approximately equal to the input fiber diameter. The focused spot on the output fiber is much smaller than the endface of the output fiber, thereby providing a substantial margin of error for mechanical misalignments. Misalignments will not cause changes in chromatic response because only large misalignments will cause the output light 32 to miss the output fiber endface. Also, the output fiber can be made much smaller than the input fiber if it is acceptable to lose a certain portion of the reflected light.

Preferably, the fibers are transparent to a very wide range of wavelengths. For example, the fibers preferably are capable of transmitting light in the wavelength range of 190–1100 nm with attenuation less than 3 dB/meter. The ability to transmit a wide range of wavelengths enables the fibers to be used in measurements where reflectance must be accurately measured over a large wavelength range, or where measurements are desired for a large number of distinct wavelengths. Suitable fibers are the PH Series, high-OH⁻ optical fibers from Meteor Optics, Inc. in Glendale Ariz.

Fibers 26, 28 are preferably mechanically flexible and therefore provide for increased mechanical flexibility of the system. For example, the mirrors 22, 24 can be moved with respect to the spectrophotometer 36 and light source 34 without changing the alignment between the mirrors and fibers 26, 28. This can be a great advantage in many applications because spectrophotometers are typically large, delicate instruments which are difficult to move, and can obstruct other instruments. Also, the ability to move the mirrors 22, 24, enables different points on the substrate to be analyzed without having to move the substrate 20. This is beneficial because in certain environments it is desirable to hold the substrate in a fixed location.

It is important to note that the chromatic response of the fibers (particularly the broad band fibers preferred in the present invention) is dependent on the shape of the fiber. Therefore, if the mirrors and fibers are moved to different locations, the chromatic response of the system is different for the different locations of the mirrors. This can cause errors when performing reflectance measurements because the changes in chromatic response can be mistakenly attributed to changes in reflectance of the substrate.

However, it is possible to compensate for these errors. This is accomplished by calibrating the spectrophotometer 36 for each position setting of the mirrors and fibers. For example, if it is desired to measure reflectance spectra at 4 locations on the substrate 20, then the spectrophotometer has 4 slightly different calibration settings. Each calibration setting is designed to compensate for differences in chromatic response in the fibers associated with the different positions. Of course, for this scheme to work, the system must be designed so that the fibers 26, 28 bend in exactly the same way every time the mirrors are moved to a certain location. This can be accomplished by enclosing the fibers in a stress-relieving jacket as known in the art.

Calibration can be provided by replacing substrate 20 with a calibration substrate having well known optical properties. For example, a silicon wafer with a thin film of $SiO_2$ having a uniform and accurately characterized thickness can be used as a calibration substrate. When the fibers 26, 28 and mirrors 22, 24 are moved across the calibration substrate (by moving the optical head 25), variations in measured reflectance spectra are entirely attributed to changes in the chromatic response of the optical system. Typically, the changes in chromatic response are mostly caused by bending of the optical fibers 26, 28. The system should be designed so that the variations in chromatic response are reproducible by repeating the movements of the fibers 26, 28 and mirrors 22, 24.

It is noted that the chromatic response of the fibers 26, 28 does not change very much if they are bent only slightly. For example, if the optical head 25 is moved up or down by a few millimeters, and the fibers are about one meter long, then the change in chromatic response is typically not great enough to warrant recalibration.

In a particularly preferred application of the present invention, reflectance measurements are used to characterize the substrate 20 according to the methods described in U.S. Pat. No. 4,905,170, herein incorporated by reference. In this method, it is preferable for reflectance measurements to be performed at normal incidence, or close to normal incidence. Therefore, it is greatly preferred for the first toroidal mirror 22 and first optical fiber 26 to be positioned so that light is incident upon the substrate at an angle as close as possible to normal. Of course, perfectly perpendicular incidence is not possible because the first and second toroidal mirrors must be spaced apart. More specifically, it is preferred for the angle of incidence to be less than about 8 degrees from normal incidence. Angles of incidence outside this range can provide unacceptably inaccurate thin film characterization, unless more complicated calculations are performed. This angle is measured from the central ray in a light cone provided by the first fiber 26 and mirror 22. It is not necessary for all the light to be within 8 degrees of normal incidence.

Figure 3:
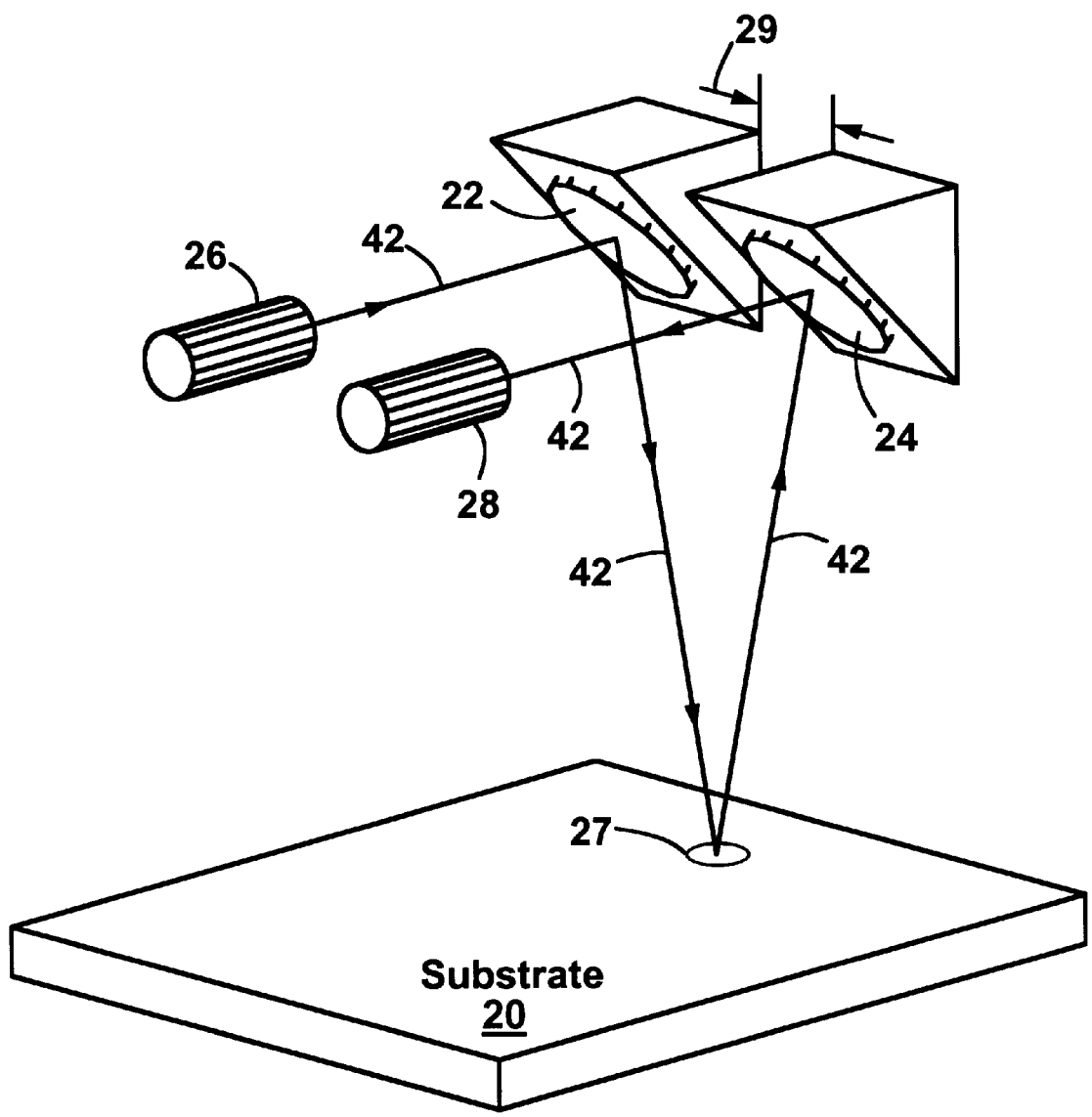
FIG. 3 shows a preferred embodiment of the present invention for performing reflectance measurements.

FIG. 3 shows another embodiment of the present invention. On-axis light path 42 is shown. Toroidal mirrors 22, 24 are located side by side. Preferably, distance 29 between mirrors 22, 24 is a small as possible so that light path 42 is nearly perpendicular to substrate 20. It is again noted that spot 27 is preferably a focused image of the endface of fiber 26. Light path 42 is a single on-axis ray. In operation, fiber 26 provides a light cone (not shown) comprising many rays which illuminate the entire spot 27.

Figure 4:
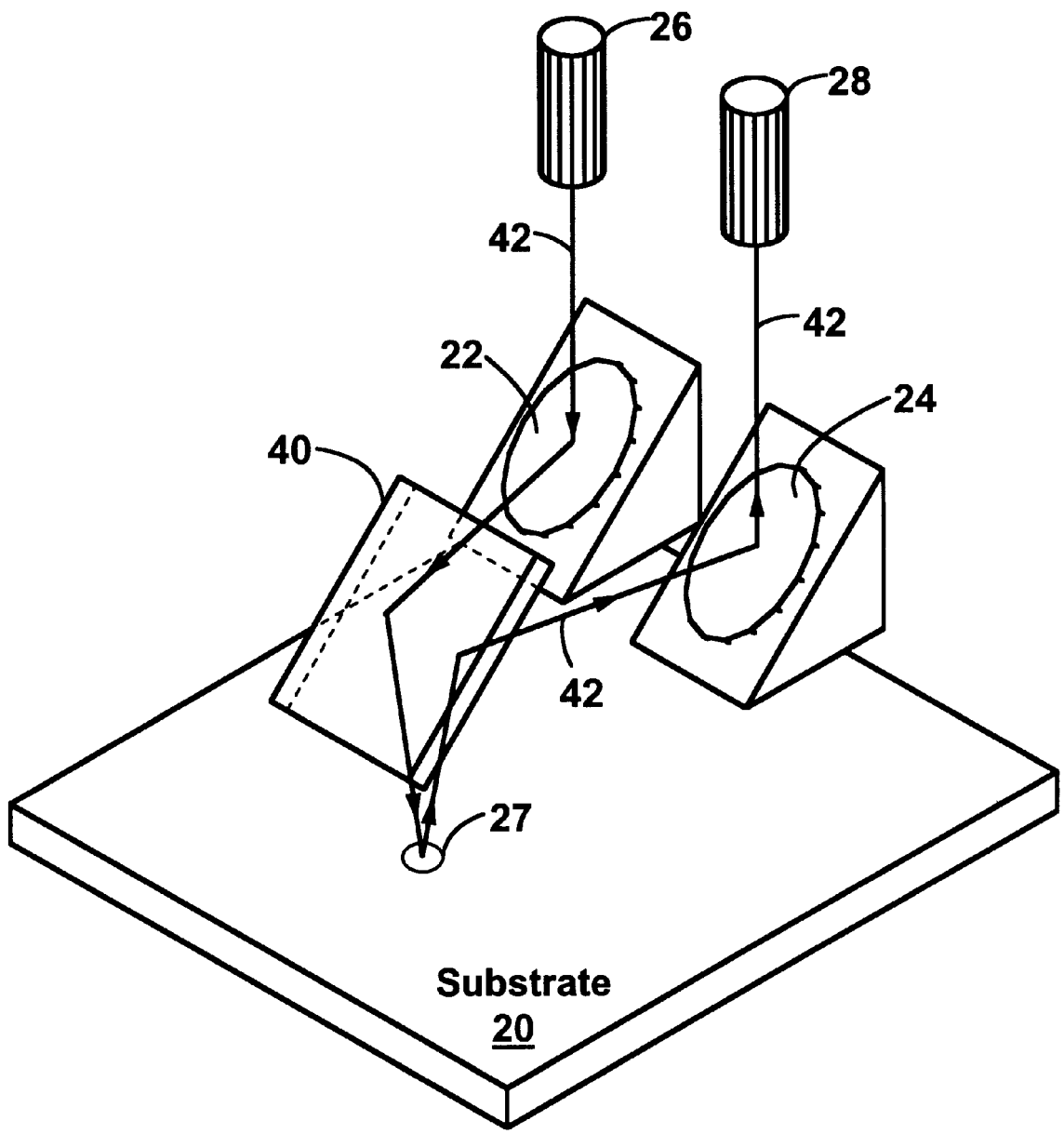
FIG. 4 shows another embodiment of the present invention having a fold mirror.

FIG. 4 shows another embodiment of the present invention having a fold mirror 40. The fold mirror 40 is located in the optical path 42 between the substrate and mirrors 22, 24. The fold mirror 40 directs input light towards the substrate 20. Spot 27 is preferably the focused image of the endface of input fiber 26. Also preferably, the fold mirror 40 is attached to the optical head 25 (not shown in FIG. 3). The mirrors 22, 24 may need to be rotated (about an axis perpendicular to substrate 20) so that on-axis light path 42 is incident upon the center of mirrors 22, 24.

Figure 5:
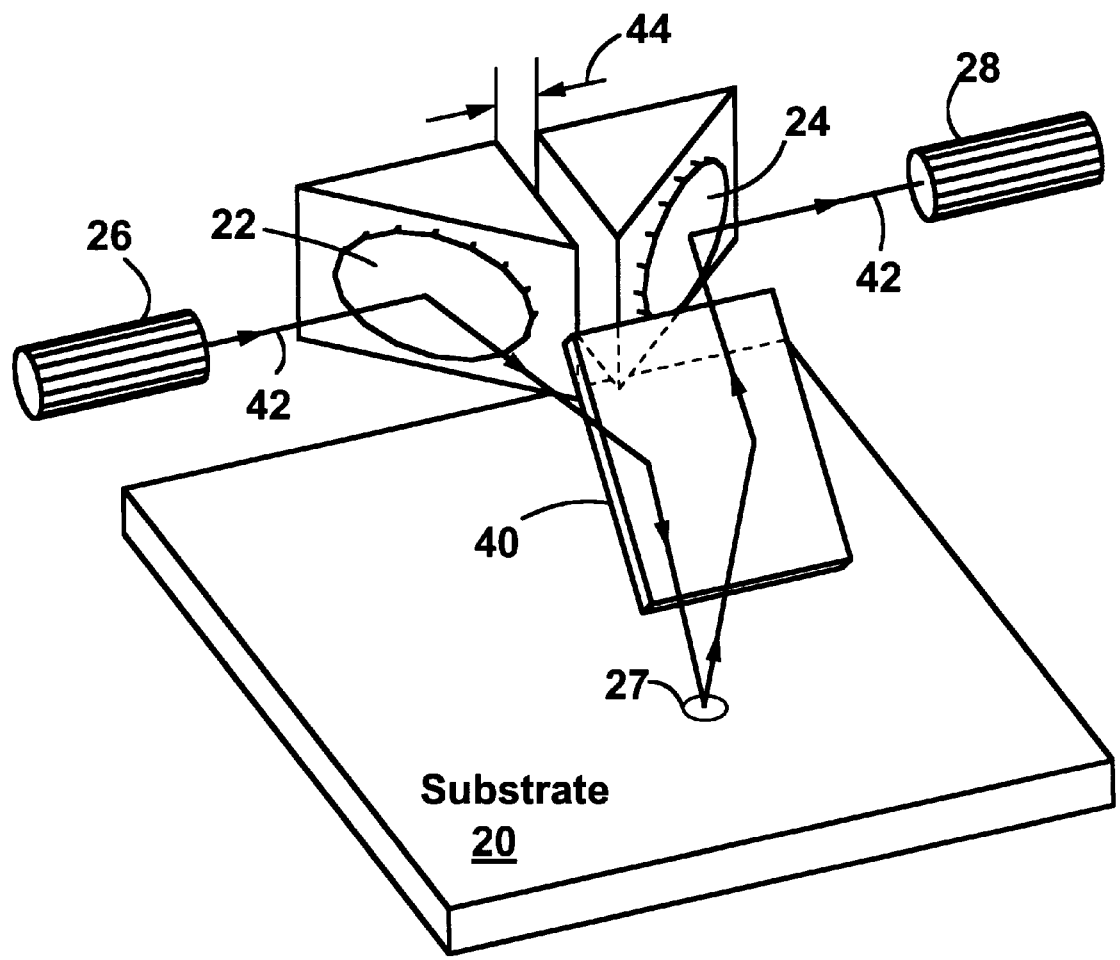
FIG. 5 shows an alternative embodiment of the present invention.

FIG. 5 shows yet another embodiment of the present invention where toroidal mirrors 22, 24 are rotated 90 degrees. Fibers 26, 28 are oriented parallel with substrate 20. The embodiment of FIG. 5 may be used in applications where there is limited space above the substrate 20. It is preferable for distance 44 to be as short as possible so that optical path is nearly perpendicular to substrate 20.

Figure 6:
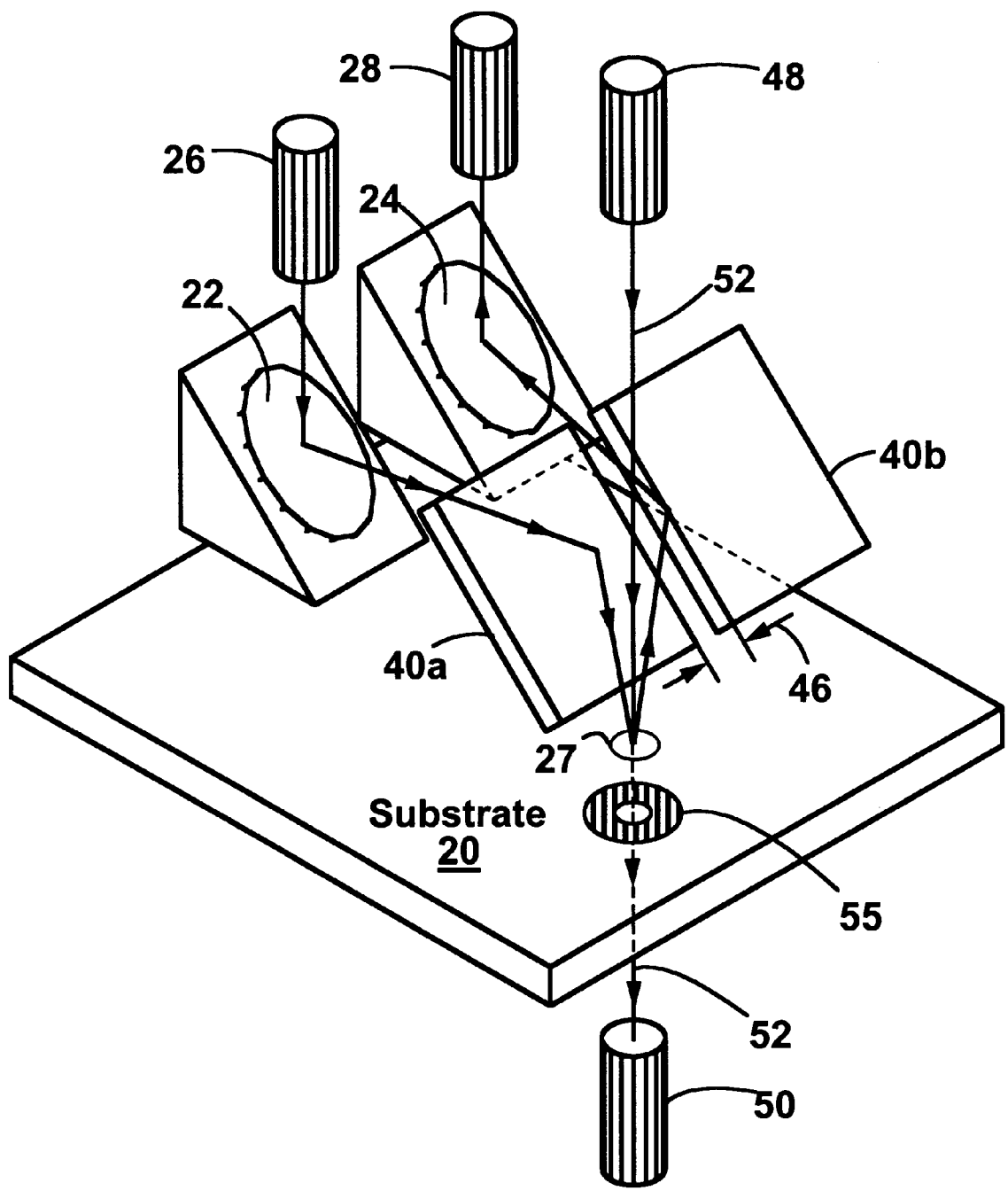
FIG. 6 shows an embodiment of the present invention for performing both reflectance and transmission measurements.

FIG. 6 shows an embodiment of the present invention for use in measuring both reflectance and transmission of the substrate 20. The system has two fold mirrors 40a, 40b which are separated by a space 46. Disposed above the space 46 is a third optical fiber 48. A fourth optical fiber 50 is located opposite the third optical fiber. The third and fourth optical fibers can be made from the same broad band optical fiber as used for first and second optical fibers. Third and fourth fibers can have the same or different core sizes. A transmission optical path 52 extends between optical fibers 48, 50. The transmission optical path 52 passes through the space 46. Preferably, the transmission optical path 52 intersects the substrate at spot 27 so that reflectance and transmission are measured at the same location. The transmission optical path 52 may include optical components such as lenses (not shown) for focusing a beam used for measuring substrate transmission. Preferably, the transmission optical path 52 has an aperture 55 located below the substrate 20. The aperture 55 assures that transmission measurements only use light incident within spot 27. Preferably, aperture 55 is located close to the bottom surface of substrate 20, e.g. within 10 millimeters of the substrate bottom surface. Preferably, fiber 48 is connected to a white light source (not shown), and fiber 50 is connected to a spectrophotometer (not shown).

In operation, reflectance and transmission measurements are preferably made simultaneously at the same location, i.e. spot 27.

Optionally, the mirrors 22, 24 and fibers 26, 28 can be rotated 90 degrees to have an arrangement like that shown in FIG. 5.

Also, third fiber 48 is optional. Third fiber 48 can be replaced with a light source and lens system. A particularly preferred light source has two incandescent bulbs and two lenses linearly arranged for independently providing visible and UV portions of the spectrum. Such broad band light sources are well known in the art and are commonly used in transmission spectrometers.

Alternatively, the two fold mirrors 40a, 40b are replaced with a single fold mirror having a hole. In this embodiment, the transmission optical path 52 extends through the hole. In the appended claims, a hole and the space 46 are understood to be included within the scope of a "gap" in the fold mirror.

Figure 7:
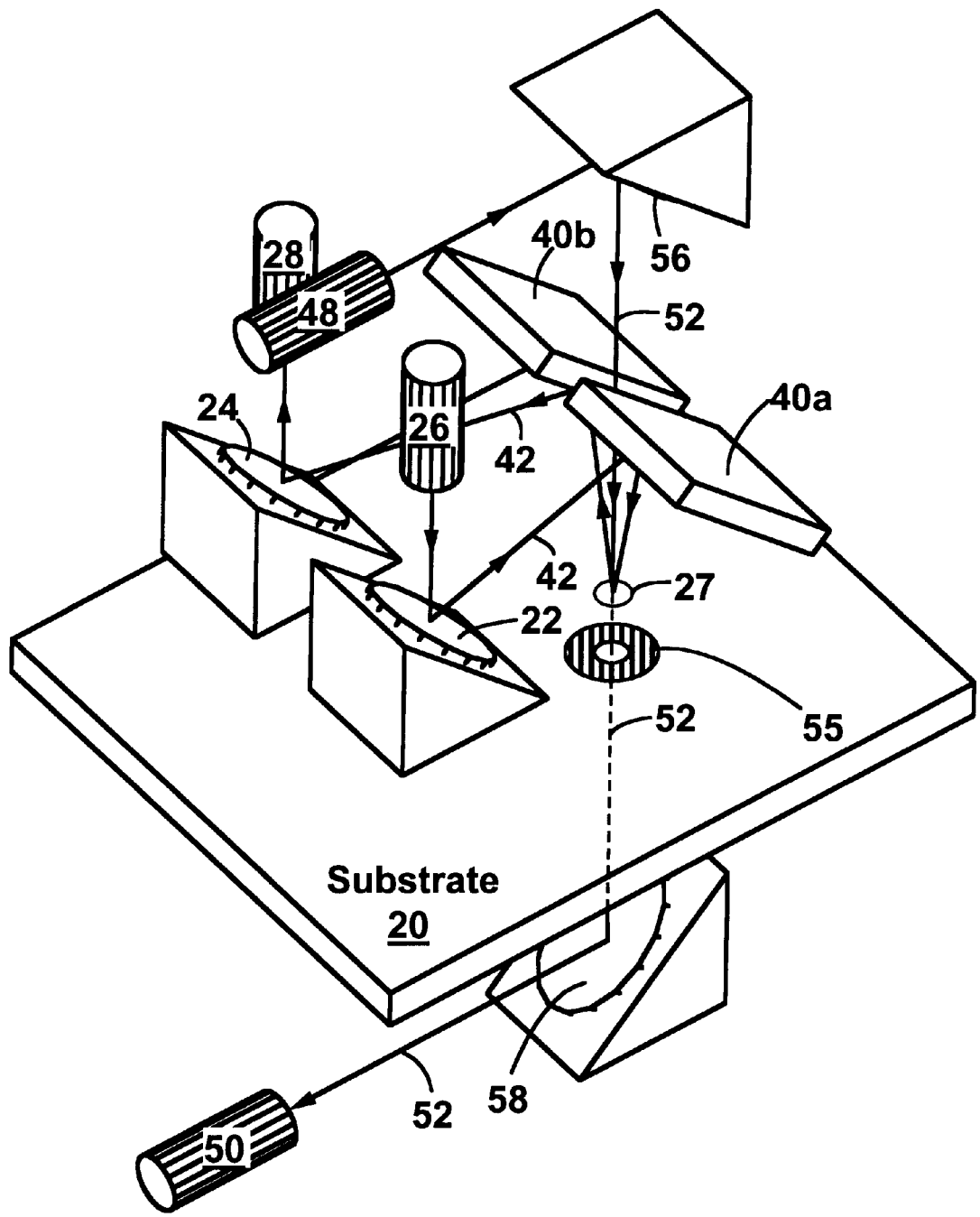
FIG. 7 shows an embodiment of the present invention for performing both reflectance and transmission measurements.

FIG. 7 shows an embodiment of the present invention having a top toroidal mirror 56 and a bottom toroidal mirror 58 disposed in the transmission optical path 52. The top toroidal mirror 56 focuses light from third fiber 48. Preferably, light from the third fiber 48 is collimated by the top toroidal mirror 56, and refocused by the bottom toroidal mirror 58 so that an image of third fiber 48 is formed on the fourth fiber endface. Light transmitted through the substrate is collected by bottom toroidal mirror and focused into fourth fiber 50. It is preferable for the system to be aligned so that optical path 42 (for measuring reflectance) and optical path 52 (for measuring transmission) strike the substrate at the same location. Preferably, all the fibers 26, 28, 48, 50, all the mirrors 22, 24, 56, 58, and the fold mirrors 40a, 40b are attached to the same optical head (not shown). Optionally, the optical head is attached to only the first and second fibers 26, 28, and first and second toroidal mirrors 22, 24. The aperture 55 can be used so that light used for measuring transmission necessarily passes through spot 27.

Figure 8:
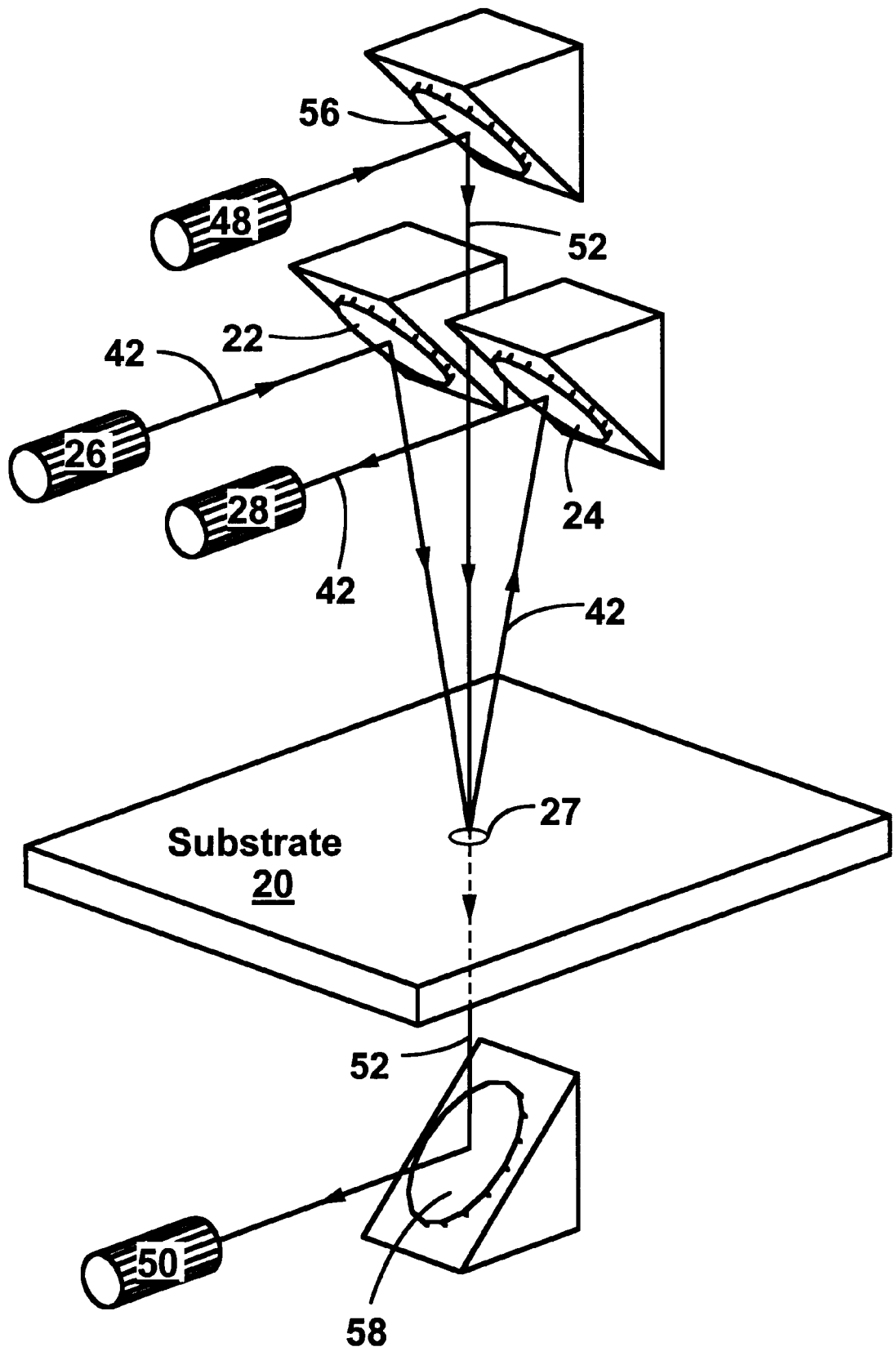
FIG. 8 shows an embodiment of the present invention for performing both reflectance and transmission measurements.

FIG. 8 shows yet another embodiment of the present invention in which the apparatus of FIG. 3 is combined with top toroidal mirror 56, bottom toroidal mirror 58, third fiber 48 and fourth fiber 50. Mirrors 56, 58 and fibers 48, 50 enable transmission measurements of the substrate to be performed at spot 27.

The present invention includes many different mechanical arrangements of mirrors and fibers for performing reflectance measurements, and, optionally, transmission measurements. Certain arrangements which have not been shown will be apparent to one skilled in the art upon reading the present disclosure, and are within the scope of the appended claims. For example, it is possible to include a gap or hole in the fold mirror 40 of FIG. 5, thereby allowing transmission measuring components to be combined with the apparatus of FIG. 5.

Also, as noted, the use of top and bottom toroidal mirrors for performing transmission measurements is optional. Refractive optics (i.e., lenses) can be used in place of the top and bottom toroidal mirrors if desired.

Figure 9:
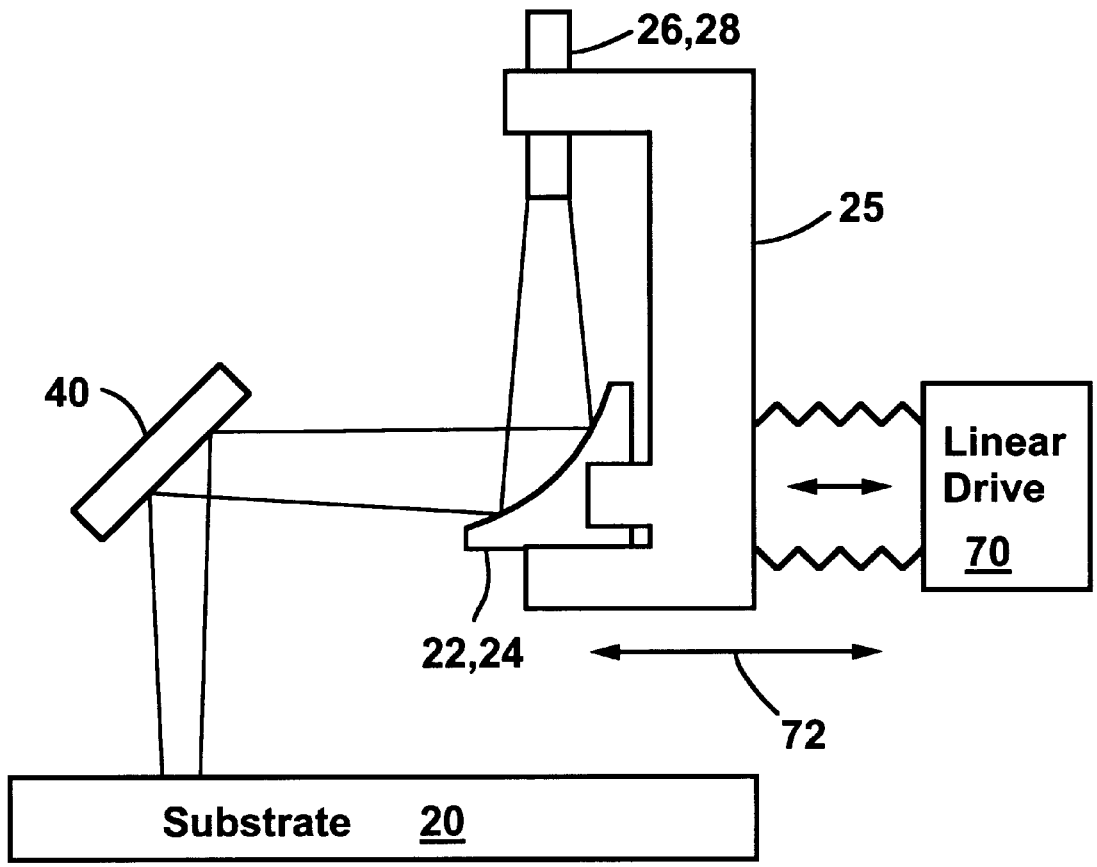
FIG. 9 shows a side view of an embodiment having a linear drive for providing focus control.

FIG. 9 shows a preferred embodiment having a fold mirror 40 and a linear drive 70 for moving the optical head 25 in a direction 72. The apparatus of FIG. 9 has generally the same arrangement of fibers 26, 28 and mirrors 22, 24 as the apparatus of FIG. 4. The fold mirror 40 is not attached to the optical head 25 and therefore cannot be moved by the drive 70. First fiber 26, second fiber 28, and both toroidal mirrors 22, 24 are attached to the optical head 25. With this arrangement, the linear drive 70 provides adjustable focusing. This is particularly beneficial in applications where substrates with different thicknesses are analyzed. The linear drive 70 can move the optical head to compensate for the different thicknesses.

Figure 10:
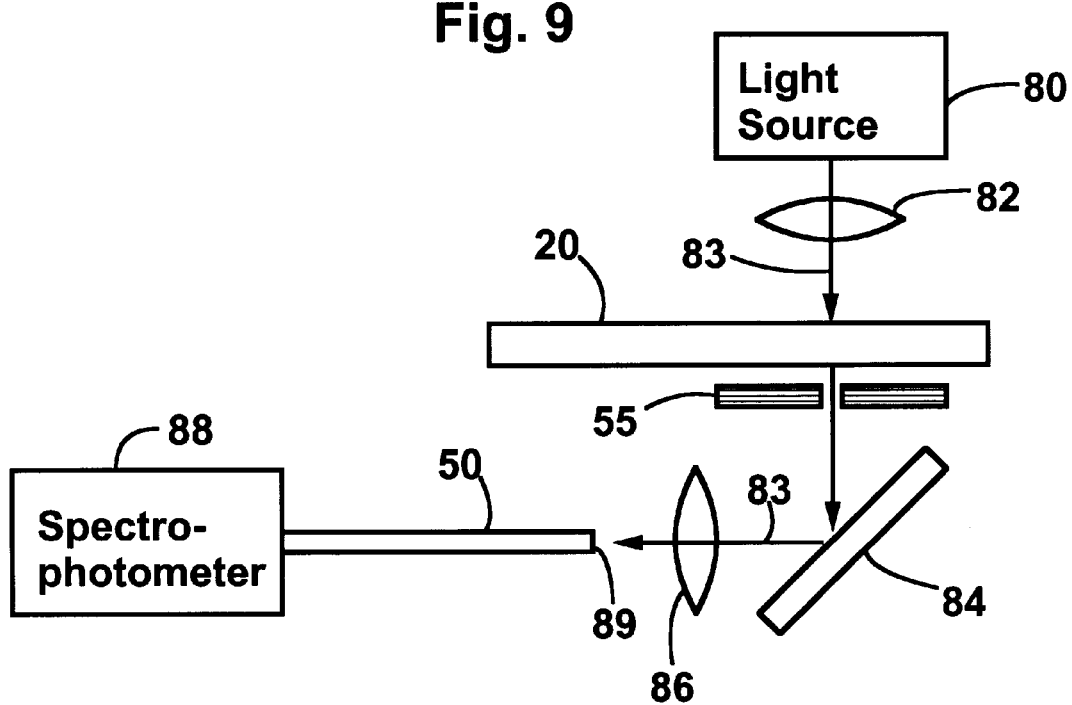
FIG. 10 shows a side view of a preferred embodiment for measuring transmission.

FIG. 10 shows a side view of transmission measuring optics according to a preferred embodiment of the present invention. A light source 80 provides broad band light beam 83 which is collimated by lens 82. The aperture 55 is located below the substrate 20. A bottom mirror 84 directs light transmitted through substrate 20 to fourth optical fiber 50. The fourth optical fiber directs transmitted light to a spectrophotometer 88. In this embodiment it is important for the transmitted light to be focused to an area on the fourth fiber endface 89 which is smaller than the core of the fourth fiber. The fiber can have a core diameter in the range of about 100–1000 microns. Optionally, a second lens 86 focuses the light into the fourth optical fiber 50.

In operation, light beam 83 is focused by lens 82, which imparts chromatic aberration into the light beam 83. As light beam 83 passes through substrate 20, the light beam suffers spherical aberration. When the light beam 83 is focused onto the endface of the fourth fiber 50, all the different wavelengths enter the fiber, although at different angles (due to the chromatic aberration of lenses). The fiber 50 is long enough so that different wavelengths are 'scrambled' within the fiber. Different wavelengths exit the fiber with essentially the same angular distribution. This scrambling effect greatly improves the chromatic response stability of the transmission measuring optics so that accurate measurements are provided by the spectrophotometer. Of course, the fiber 50 must be long enough to effectively scramble the wavelengths. Additionally, the fiber 50 must be short enough so that far ultraviolet and far infrared wavelengths are not excessively attenuated. Preferably, the fiber 50 is at least 10 cm long. More preferably, the fiber 50 is about 1–2 meters long. The PH series, high OH⁻ optical fiber from Meteor Optics can be used.

The present invention provides systems for measuring reflectance having a very stable chromatic response. The toroidal mirrors produce no chromatic aberration, and therefore generally do not cause variations in chromatic response when slightly misaligned.

It will be clear to one skilled in the art that the above embodiment may be altered in many ways without departing from the scope of the invention. Accordingly, the scope of the invention should be determined by the following claims and their legal equivalents.

What is claimed is:

1. An optical system for performing broad band reflectance measurements of a substrate surface, the system comprising:

a) a first optical fiber;

b) a first toroidal mirror for receiving a light beam from the first optical fiber and directing the light beam toward the substrate surface so that the light beam reflects from a spot on the substrate surface;

c) a second optical fiber;

d) a second toroidal mirror for receiving the light beam after reflecting from the substrate surface and directing the light beam into the second optical fiber; and e) a means for performing transmission measurements at the spot where the light beam is incident upon the substrate surface.

2. The system of claim 1 wherein the first toroidal mirror is spaced apart from the first optical fiber and substrate such that an image of the first optical fiber is formed on the substrate.

3. The system of claim 1 wherein the first and second optical fibers have a core diameter in the range of 100–1000 microns.

4. The system of claim 1 wherein the first and second optical fibers transmit light within the wavelength range of 190–1100 nanometers with an attenuation less than 5 dB/meter.

5. The system of claim 1 wherein the first fiber has a core diameter larger than a core diameter of the second fiber.

6. The system of claim 1 wherein the second fiber has a core diameter larger than a core diameter of the first fiber.

7. The system of claim 1 wherein the first toroidal mirror is oriented such that light is incident upon the substrate surface at an angle within 8 degrees of normal incidence.

8. The system of claim 1 wherein the means for performing transmission measurements comprises a top toroidal mirror above the substrate and a bottom toroidal mirror below the substrate.

9. The system of claim 1 further comprising an aperture disposed below the substrate and aligned with the spot.

10. The system of claim 1 wherein the means for performing transmission measurements comprises a third optical fiber located below the substrate for receiving light transmitted by the substrate.

11. The system of claim 1 wherein the means for performing transmission measurements comprises a third optical fiber and a lens for focusing light into the third fiber, wherein the third fiber is at least 10 centimeters long, and wherein the third fiber has a core diameter in the range of 100–1000 microns.

12. The system of claim 1 further comprising a computer for calculating optical constants n and k of the substrate.

13. An optical system for performing broad band reflectance measurements of a substrate surface, the system comprising:

a) a first optical fiber;

b) a planar fold mirror oriented non-planar parallel with respect to the substrate surface;

c) a first toroidal mirror for receiving a first light beam from the first optical fiber and directing the first beam toward the fold mirror such that:
  i) the fold mirror directs the first beam toward a spot on the substrate surface, and
  ii) the fold mirror receives the first beam after reflecting from the spot on the substrate surface;

d) a second optical fiber;

e) a second toroidal mirror for receiving the first beam after reflecting from the substrate surface and the fold mirror and for directing the first beam into the second optical fiber.

14. The system of claim 13 wherein the first toroidal mirror is spaced apart from the first optical fiber such that an image of the first optical fiber is formed on the substrate surface.

15. The system of claim 13 wherein the first and second optical fibers have a core diameter in the range of 100–1000 microns.

16. The system of claim 13 wherein the first and second optical fibers transmit light within the wavelength range of 190–1100 nanometers with an attenuation less than 5 dB/meter.

17. The system of claim 13 wherein the first toroidal mirror and fold mirror are oriented such that the first beam is incident upon the substrate surface at an angle within 8 degrees of normal incidence.

18. The system of claim 13 wherein the fold mirror is oriented 35–55 degrees with respect to the substrate surface.

19. The system of claim 13 wherein the fold mirror has a gap for transmitting a second light beam directed toward the substrate surface.

20. The system of claim 19 wherein the gap is located such that the second light beam is incident upon the substrate surface at the same location as the first light beam.

21. The system of claim 13 further comprising a means for performing transmission measurements at the spot where the first light beam is incident upon the substrate surface.

22. The system of claim 21 wherein the means for performing transmission measurements comprises a top toroidal mirror above the substrate and a bottom toroidal mirror below the substrate.

23. The system of claim 21 further comprising an aperture disposed below the substrate and aligned with the spot.

24. The system of claim 21 wherein the means for performing transmission measurements comprises a third optical fiber located below the substrate for receiving light transmitted by the substrate.

25. The system of claim 21 wherein the means for performing transmission measurements comprises a third optical fiber and a lens for focusing light into the third optical fiber, wherein the third fiber is at least 10 centimeters long, and wherein the third fiber has a core diameter in the range of 100–1000 microns.

26. The system of claim 13 further comprising a linear drive for moving the first optical fiber, the second optical fiber, the first toroidal mirror, and the second toroidal mirror with respect to the fold mirror, whereby adjustable focus control is provided.

27. The system of claim 13 wherein the first optical fiber and second optical fiber are oriented parallel with the substrate surface.

28. The system of claim 13 wherein the first fiber has a core diameter larger than a core diameter of the second fiber.

29. The system of claim 13 wherein the second fiber has a core diameter larger than a core diameter of the first fiber.

30. The system of claim 13 further comprising a computer for calculating optical constants n and k of the substrate.

* * * * *